US009453046B2

(12) United States Patent
Meyer et al.

(10) Patent No.: US 9,453,046 B2
(45) Date of Patent: Sep. 27, 2016

(54) ACTIVATED CARBON FILTRATION FOR PURIFICATION OF BENZODIAZEPINE ADCS

(71) Applicant: Seattle Genetics, Inc., Bothell, WA (US)

(72) Inventors: Damon Meyer, Bellevue, WA (US); Michael Sun, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 14/774,348

(22) PCT Filed: Mar. 12, 2014

(86) PCT No.: PCT/US2014/024058
§ 371 (c)(1),
(2) Date: Sep. 10, 2015

(87) PCT Pub. No.: WO2014/143622
PCT Pub. Date: Sep. 18, 2014

(65) Prior Publication Data
US 2016/0039870 A1 Feb. 11, 2016

Related U.S. Application Data

(60) Provisional application No. 61/780,131, filed on Mar. 13, 2013, provisional application No. 61/782,156, filed on Mar. 14, 2013, provisional application No. 61/890,067, filed on Oct. 11, 2013.

(51) Int. Cl.

| | |
|---|---|
| ***C07K 19/00*** | (2006.01) |
| ***C07K 1/34*** | (2006.01) |
| ***B01D 15/08*** | (2006.01) |
| ***C07D 487/04*** | (2006.01) |
| ***C07D 519/00*** | (2006.01) |
| ***C07K 16/00*** | (2006.01) |
| ***C07K 16/28*** | (2006.01) |
| ***A61K 31/5517*** | (2006.01) |
| ***A61K 47/48*** | (2006.01) |

(52) U.S. Cl.
CPC ............ *C07K 1/34* (2013.01); *A61K 31/5517* (2013.01); *A61K 47/48384* (2013.01); *A61K 47/48561* (2013.01); *B01D 15/08* (2013.01); *C07D 487/04* (2013.01); *C07D 519/00* (2013.01); *C07K 16/00* (2013.01); *C07K 16/2803* (2013.01); *C07K 2317/51* (2013.01); *C07K 2317/53* (2013.01)

(58) Field of Classification Search
CPC ...................................................... C07K 19/00
See application file for complete search history.

(56) References Cited

U.S. PATENT DOCUMENTS

| | | | |
|---|---|---|---|
| 8,697,688 | B2 | 4/2014 | Howard et al. |
| 8,940,733 | B2 | 1/2015 | Howard et al. |
| 2005/0032243 | A1 | 2/2005 | Pollack |
| 2012/0189605 | A1 | 7/2012 | Koppaka et al. |
| 2013/0028919 | A1 | 1/2013 | Howard et al. |
| 2014/0274907 | A1 | 9/2014 | Howard et al. |
| 2014/0286970 | A1 | 9/2014 | Jeffrey et al. |
| 2014/0302066 | A1 | 10/2014 | Jeffrey |

FOREIGN PATENT DOCUMENTS

| | | |
|---|---|---|
| EP | 0665020 | 1/1995 |
| EP | 1473301 | 11/2004 |
| WO | 2007/105027 | 9/2007 |
| WO | 2011/130613 | 10/2011 |
| WO | 2013/028330 | 2/2013 |

OTHER PUBLICATIONS

PD-10 Desalting Columns, GE Healthcare, Instructions 52-1308-00BB, 2007.

Lee et al., "Evaluation of Drugs for Suicide Attempt and Antidote Uses in Emergency Room of a Hospital in Korea," Kor. J. Clin. Pharm. 22(4):304-315, 2012.

*Primary Examiner* — Bruck Kifle
(74) *Attorney, Agent, or Firm* — Seattle Genetics, Inc.

(57) ABSTRACT

Disclosed are methods of purifying mixtures comprising benzoidiazepine antibody-drug conjugates.

21 Claims, 4 Drawing Sheets

ACTIVATED CARBON FILTRATION FOR PURIFICATION OF BENZODIAZEPINE ADCS

This application is a national stage filing under 35 U.S.C. 371 of International Application No. PCT/US2014/024058 filed Mar. 12, 2014, and claims the benefit of U.S. Provisional Application Nos. 61/780,131 filed Mar. 13, 2013, 61/782,156 filed Mar. 14, 2013, and 61/890,067 filed Oct. 11, 2013, each of which is incorporated by reference in its entirety herein.

BACKGROUND

Antibody-drug conjugates (ADCs) can provide an effective means of delivering a drug to a targeted site in a tissue or organism. Recognition of a target such as a tumor by the antibody minimizes exposure of non-target tissues to toxic chemotherapeutic agents and limits adverse effects associated with the toxicity of "free" drugs (i.e., unbound to a carrier such as an antibody). ADCs can be prepared by a number of techniques. Prior to administration to a human or other subject, the conjugate is purified to remove free drugs and other impurities.

Due to the very high potency of benzodiazepine containing drugs, the removal of free drug-related impurities from a mixture comprising benzodiazepine ADCs and benzodiazepine drug-related impurities needs be highly effective. The present invention addresses this and other needs.

GENERAL

Figure 1:
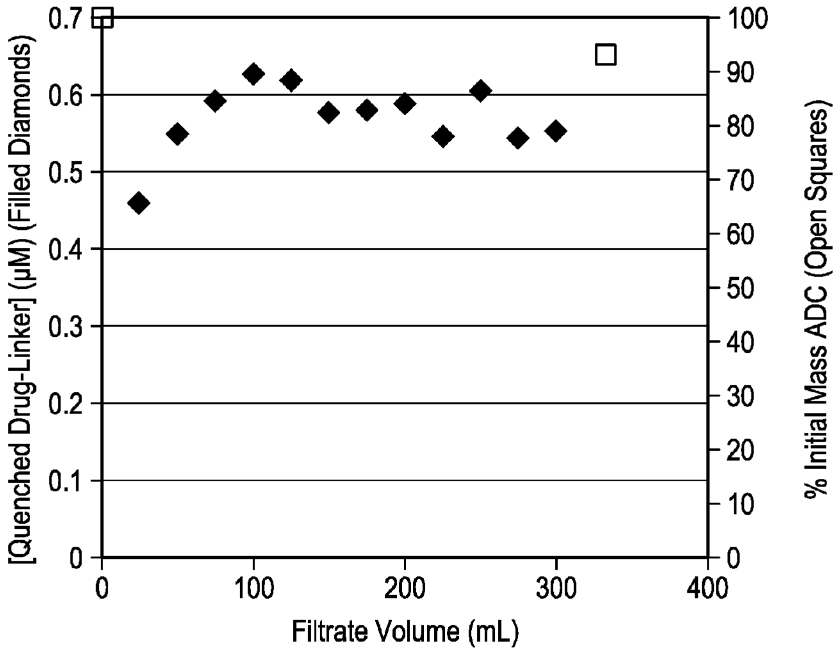
FIG. 1 provides a graph showing the concentration of quenched PBD drug-linker in the quenched conjugation reaction mixture following filtration through a Grade 5 3M Purification activated charcoal filter. The data demonstrates an approximately 60 fold reduction in quenched drug-linker level, with the maximum capacity of the filter not being reached. Filled diamonds represent the quenched drug-linker and the unfilled squares represent the ADC recovery.

The present invention is based, in part, on the discovery that many of the commonly employed methods for separating drug-related impurities from antibody-drug conjugate mixtures (e.g., tangential flow filtration) are unable to remove benzodiazepine drug-related impurities from mixtures comprising benzodiazepine ADCs and benzodiazepine drug-related impurities to an acceptable low level. It was surprisingly found that the benzodiazepine drug-related impurities could be effectively removed by filtration with activated charcoal. It was further discovered that re-circulation over an activated charcoal filter or multiple discrete filtrations using the same filter could further reduce the benzodiazepine drug-related impurities without having a negative impact on benzodiazepine ADC recovery.

SUMMARY

Provided herein are methods for removing benzodiazepine drug-related impurities from mixtures comprising benzodiazepine ADCs and benzodiazepine drug-related impurities by filtration with activated charcoal. Activated charcoal filtration can be performed by passing a mixture comprising benzodiazepine ADCs and benzodiazepine drug-related impurities through an activated charcoal filter. Accordingly, in some aspects, the present invention provides a method for removing benzodiazepine drug-related impurities from mixtures comprising benzodiazepine ADCs and benzodiazepine drug-related impurities comprising the step of passing the mixture comprising through an activated charcoal filter (e.g., a filter in which activated charcoal is impregnated on a cellulose solid support or other type of solid support). Carbon filtration can also be performed, for example, by adding bulk activated charcoal, either as a powder, or as a suspension, to the mixture to be purified, mixing and or incubating the mixture, then removing the activated charcoal to which the impurity is adsorbed. Accordingly, in some aspects, the present invention provides a method for removing benzodiazepine drug-related impurities from mixtures comprising benzodiazepine ADCs and benzodiazepine drug-related impurities comprising the step of contacting the mixture comprising benzodiazepine ADCs and benzodiazepine drug-related impurities with bulk activated carbon and passing the mixture through a filter. In some aspects, the bulk activated carbon is in powder form. In other aspects, the bulk activated charcoal is a suspension. In all of the above methods, filtration can be via single pass filtration, multiple discrete filtrations through a single filter, or recirculation through a single filter. In embodiments wherein filtration is via multiple discrete filtrations through a single filter, 2 or more discrete filtrations can be performed. For example, 2 discrete filtrations can be performed, 3 discrete filtrations can be performed, or 3 or more discrete filtrations can be performed. In embodiments wherein filtration is via recirculation, the recirculation can be continuous. In some aspects, the mixture comprising the ADCs and impurities is recirculated from 3 to about 20 times through the filter.

Provided herein are methods for removing benzodiazepine drug-related impurities from mixtures comprising benzodiazepine ADCs and benzodiazepine drug-related impurities comprising passing a mixture comprising benzodiazepine ADCs and benzodiazepine drug-related impurities through a single activated charcoal filter multiple times to yield a purified solution of benzodiazepine ADCs. The mixture can be recirculated through the filter. Alternatively, the multiple passes through the filter can be multiple discrete passages through the filter. Also provided herein are methods for removing benzodiazepine drug-related impurities from mixtures comprising benzodiazepine ADCs and benzodiazepine drug-related impurities by contacting a mixture comprising benzodiazepine ADCs and benzodiazepine drug-related impurities with activated charcoal and passing the mixture through a single filter multiple times to yield a purified solution of benzodiazepine ADCs. The mixture can be recirculated through the filter. Alternatively, the multiple passes through the filter can be multiple discrete passages through the filter. In preferred embodiments, the purified solution of benzodiazepine ADCs will have a concentration of benzodiazepine drug-related impurities of about 1 μM or less, preferably 0.2 μM, or even 0.1 μM or less. In preferred embodiments, the purified solution of benzodiazepine ADCs will have a concentration of quenched drug-linkers of about 1 μM or less, preferably 0.2 μM, or even 0.1 μM or less.

In preferred aspects, the benzodiazepine drug-related impurities that are removed from the mixture are quenched drug-linkers.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic.

The term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Carbocycles preferably have 3 to 8 carbon ring atoms.

The phrase "pharmaceutically acceptable salt," as used herein, refers to pharmaceutically acceptable organic or inorganic salts of a compound. The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The term "antibody" is used herein to denote immunoglobulin proteins produced by the body in response to the presence of an antigen and that bind to the antigen, as well as antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as $F(ab')_2$ and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen.

The term "genetically engineered antibodies" or "engineered antibody" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362:367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')$_2$, F(ab)c, diabodies, dAbs, minibodies, nanobodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least 85%, at least 90%, at least 95%, or 100% of corresponding residues defined by Kabat are identical. Hence, all parts of a humanized antibody, except possibly the CDRs, are entirely or substantially from corresponding parts of natural human immunoglobulin sequences.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

An antibody-drug conjugate (ADC) is an antibody conjugated to a cytotoxic drug typically via a linker. The linker may comprise a cleavable unit or may be non-cleavable. Cleavable units include, for example, disulfide containing linkers that are cleavable through disulfide exchange, acid-labile linkers that are cleavable at acidic pH, and linkers that are cleavable by hydrolases, esterases, peptidases, and glucoronidases (e.g., peptide linkers and glucoronide linkers). Non-cleavable linkers are believed to release drug via a proteolytic antibody degradation mechanism.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an ADC for the treatment of cancer, administration into the systemic circulation by intravenous or subcutaneous administration may be desired. For treatment of a cancer characterized by a solid tumor, administration can be localized directly into the tumor.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited.

Reference to a numerical range herein (e.g., "X to Y" or "from X to Y") includes the endpoints defining the range and all values falling within the range.

Unless otherwise apparent from the context, when a value is expressed as "about" X or "approximately" X, the stated value of X will be understood to be accurate to ±10%.

Benzodiazepine Antibody-Drug Conjugates

A benzodiazepine antibody-drug conjugate refers to an antibody conjugated to a benzodiazepine dimer typically, although not necessarily, via a linker. A benzodiazepine drug-linker refers to a benzodiazepine dimer attached to a linker. A benzodiazepine compound has at its core a benzene ring fused to a diazepine ring. Exemplary ring structures for the benzene ring fused to a diazepine ring are as follows:

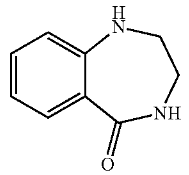

3,4-dihydro-1H-benzo[e][1,4]diazepin-5(2H)-one

-continued

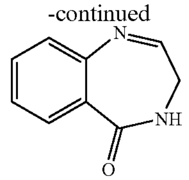

3H-benzo[e][1,4]diazepin-5(4H)-one

Benzodiazepine compounds differ in the number, type and position of substituents on both rings and in the degree of saturation of the diazepine ring. They also differ in the number of additional rings fused to the benzene and/or diazepine ring. Included within the definition of benzodiazepine compounds are those in which the benzene or diazepine ring is fused to one or more aromatic or non-aromatic carbocyclic or heterocyclic rings. A benzodiazepine dimer is a compound that has been formed by joining two benzodiazepine units together, via a tether.

The antibody component of the benzodiazepine antibody-drug conjugate can be conjugated to one or more benzodiazepine drug-linkers e.g., 1 to 20 drug-linkers. In some aspects, the antibody component of the benzodiazepine antibody-drug conjugate will be conjugated to 1, 2, 3, or 4 drug-linkers. Conjugation can be via different positions on the antibody. In some aspects, conjugation will be via a sulfur atom of a cysteine residue. In some aspects the cysteine residue is a cysteine residue of the interchain disulfides of the antibody. In other aspects, the cysteine residue is engineered into the antibody. In some aspects, the cysteine residue is engineered into the antibody at position 239 (human IgG1) as determined by the EU index (Kabat, *Sequences of Proteins of Immunological Interest* (National Institutes of Health, Bethesda, Md., 1987 and 1991)). In some aspects, there will be an average 2 drug-linkers per antibody in a benzodiazepine ADC mixture or formulation and the drug-linkers will be conjugated to a cysteine residue introduced into the antibody at position 239 (human IgG1) as determined by the EU index (Kabat, *Sequences of Proteins of Immunological Interest* (National Institutes of Health, Bethesda, Md., 1987 and 1991)).

In one aspect, the benzodiazepine dimer is a pyrrolobenzodiazepine (PBD) dimer. PBDs are of the general structure:

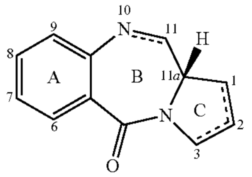

PBDs differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine ether (NH—CH(OR)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumour agents. The biological activity of these molecules can be potentiated by joining two PBD units together, (e.g., through C8/C'-hydroxyl functionalities via a flexible alkylene linker). The PBD dimers are thought to form sequence-selective DNA lesions such as the palindromic 5'-Pu-GATC-Py-3' interstrand cross-link which is thought to be mainly responsible for their biological activity.

Exemplary PBD dimers to be used as conjugates are as follows:

PBD Dimer 1

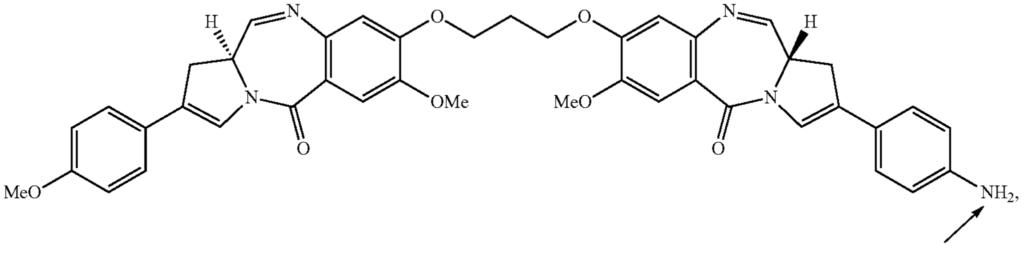

PBD Dimer 2

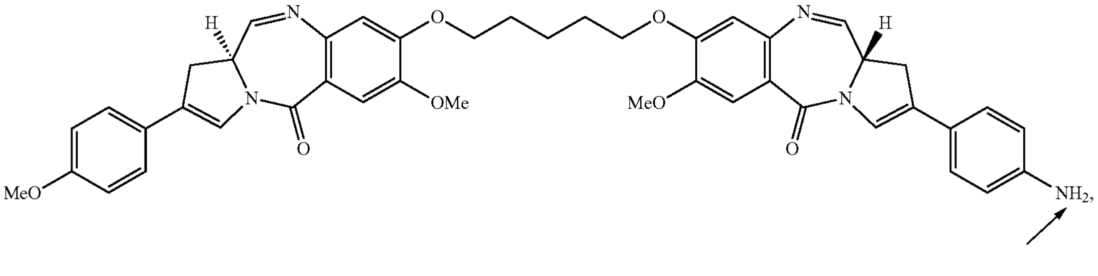

-continued
PBD Dimer 3
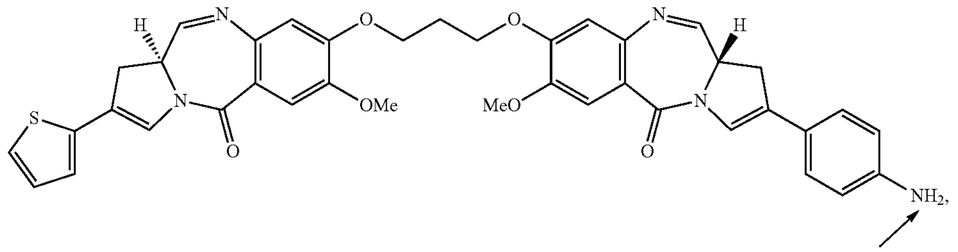
PBD Dimer 4
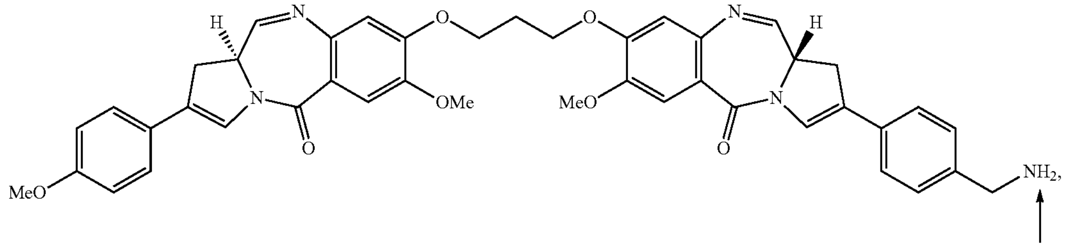
PBD Dimer 5
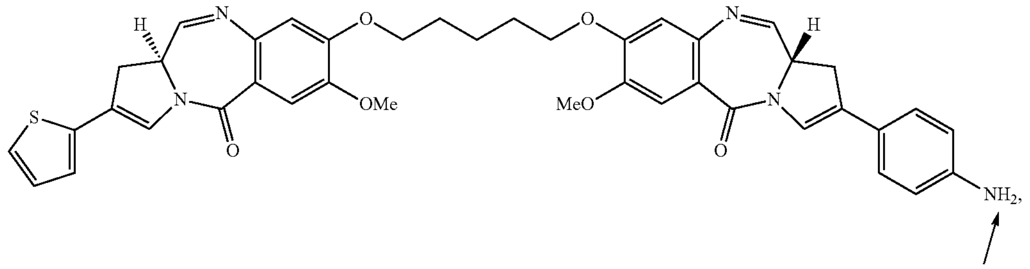
PBD Dimer 6
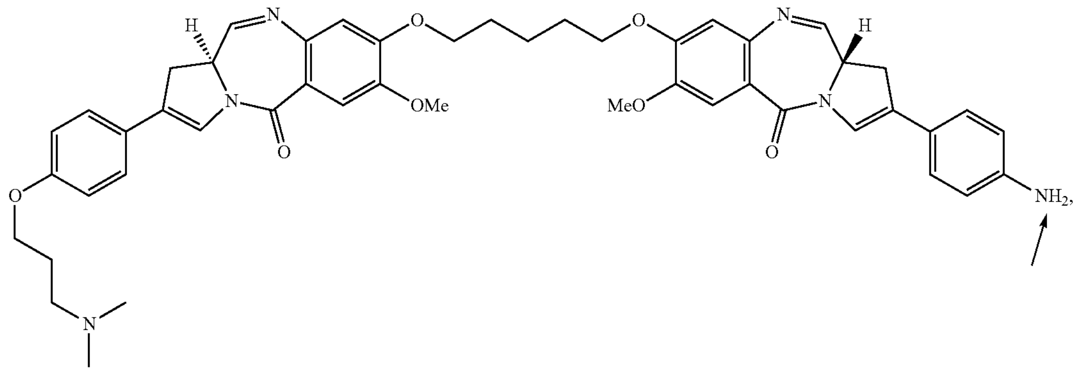
PBD Dimer 7
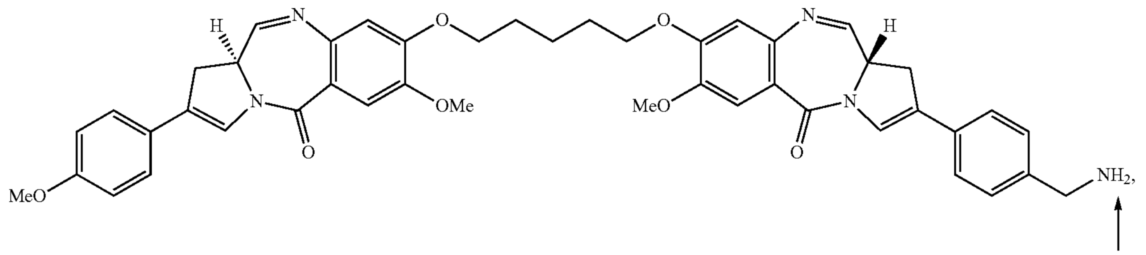

-continued
PBD Dimer 8
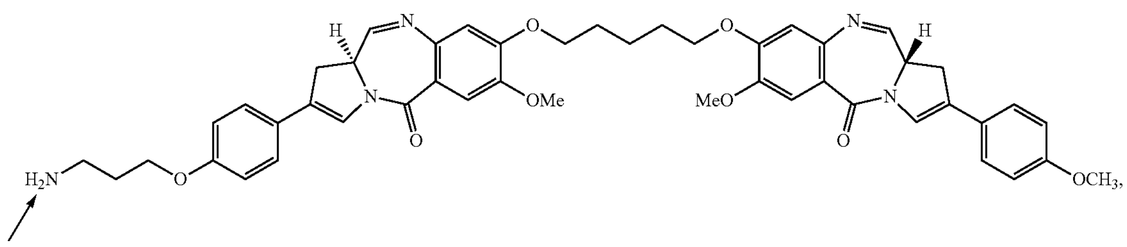
PBD Dimer 9
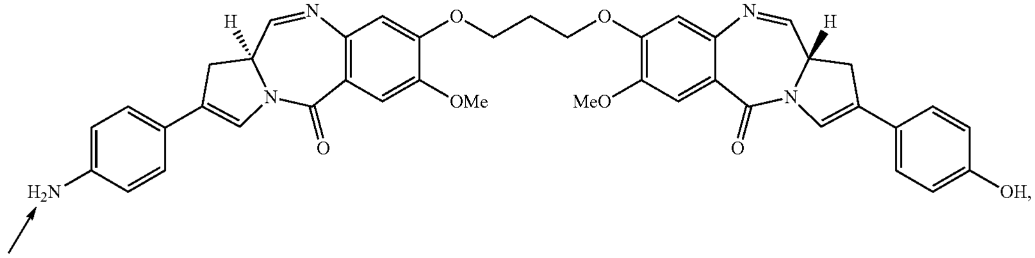
PBD Dimer 10
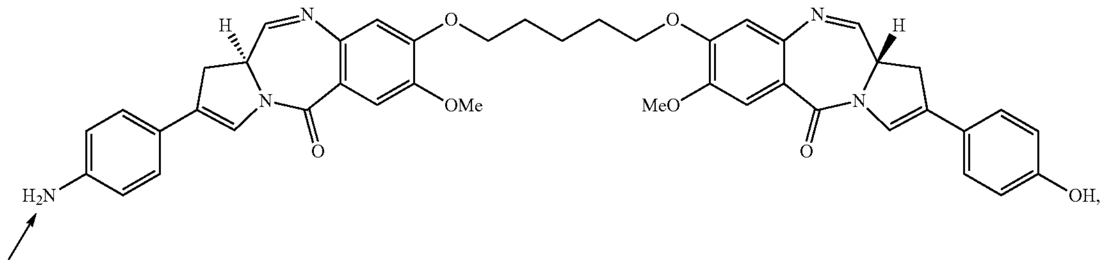
PBD Dimer 11
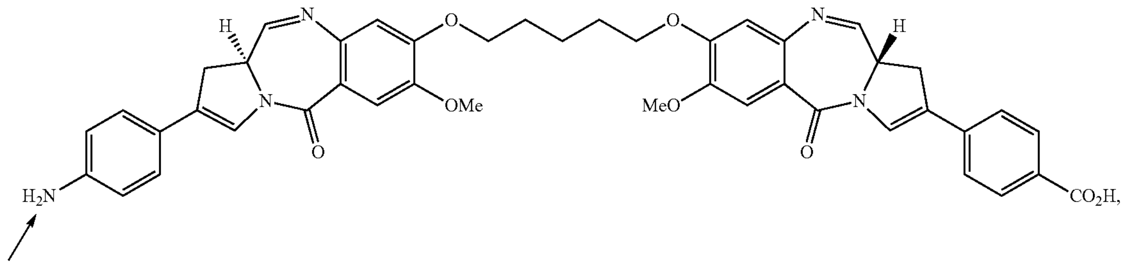
PBD Dimer 12
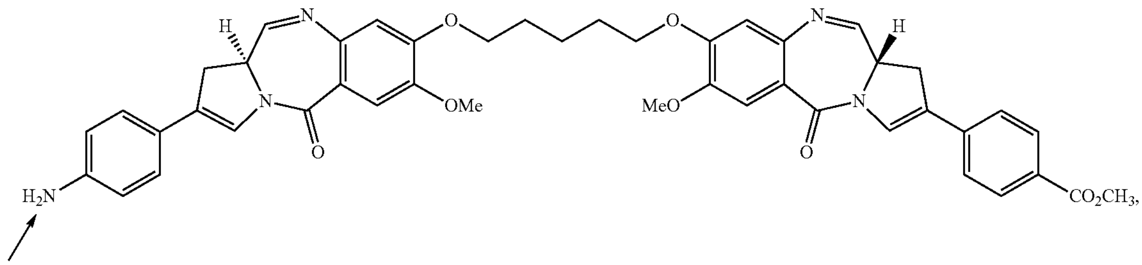

-continued

PBD Dimer 13

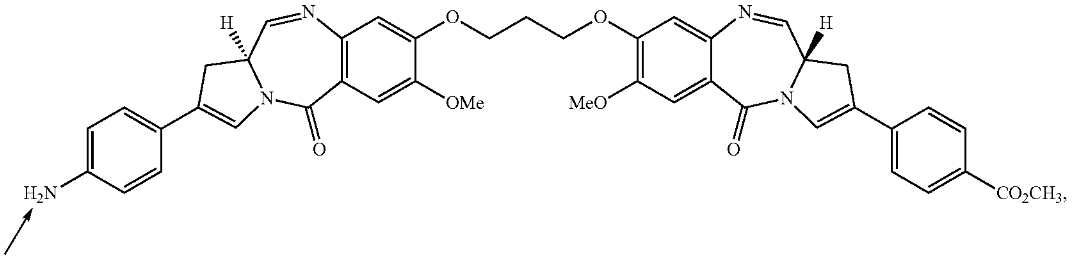

PBD Dimer 14

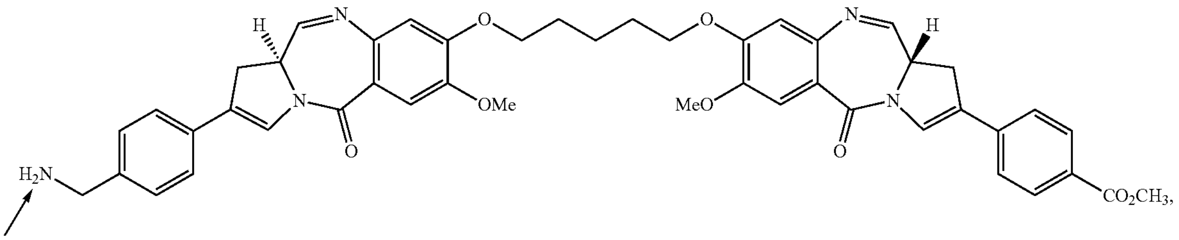

PBD Dimer 15

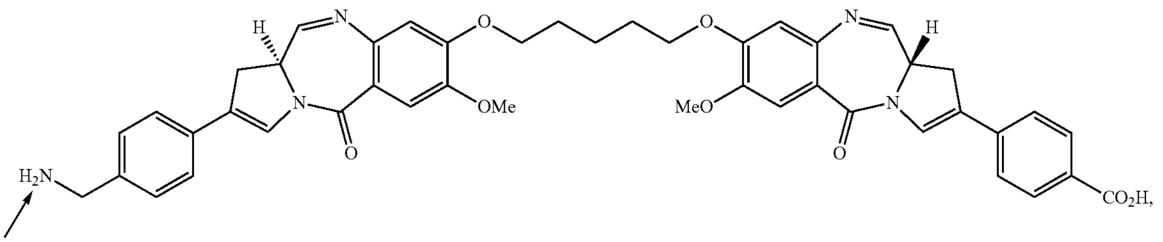

PBD Dimer 16

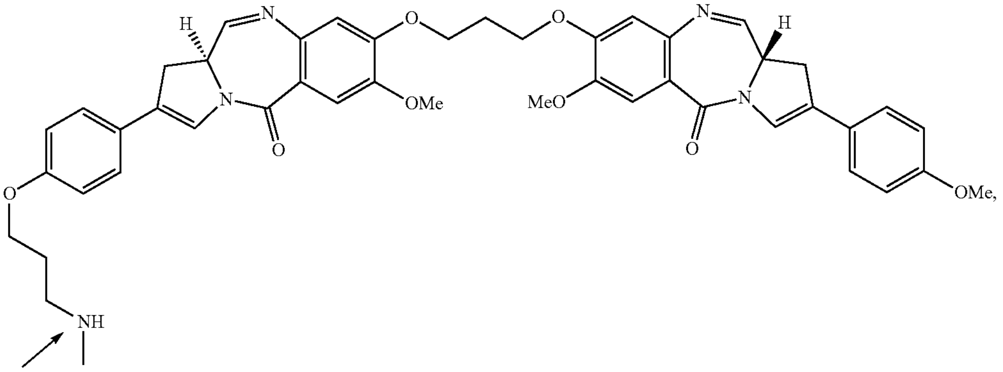

or

PBD Dimer 17

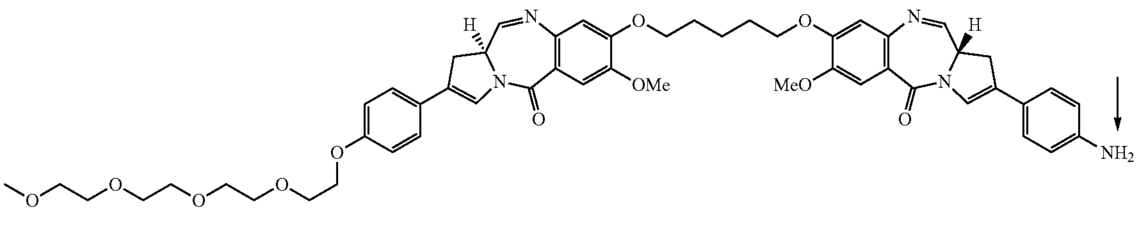

or a salt thereof (e.g., pharmaceutically acceptable salt).

The PBD dimer can be linked to the antibody at any position suitable for conjugation to a linker. For example, in some embodiments, the PBD dimer will have a substituent at the C2 position (e.g., a primary or secondary amine) that provides an anchor for linking the compound to the antibody. The C2 position is marked by an arrow in the exemplary structures shown above. In alternative embodiments, the N10 position of the PBD dimer will provide the anchor for linking the compound to the antibody.

In another aspect, the benzodiazepinedimer drug is an indolinobenzodiazepine dimer or an oxazolidinobenzodiazepine dimer. Indolinobenzodiazepines (IBDs) and oxazolidinobenzodiazepines (OBDs) are of the general structure:

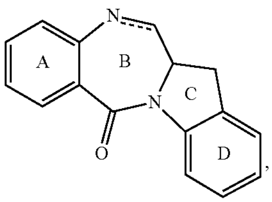
,

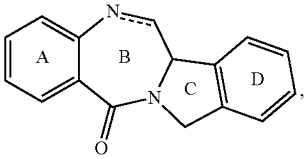
, and

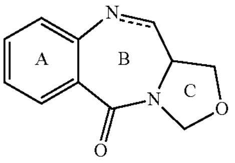

a target substrate for an enzyme) or a non-cleavable linker (e.g., linker released by degradation of the antibody). The linker may further comprise a maleimide group for linkage to the antibody, e.g., maleimidocaproyl. PBD dimers, IBD dimers, OBD dimers, linkers, and conjugates thereof are known in the art. See for example, WO 2010/091150, WO 2012/112708, WO 2012/128868, WO 2011/023883, and WO 2009/016516.

An exemplary linker for use with the benzodiazepine drugs, including any of those described herein, is as follows wherein the wavy line indicates the site of attachment to the drug and the antibody is linked via the maleimide group.

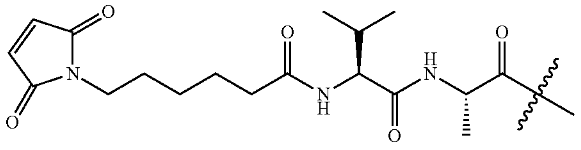 [SMILES: *C(=O)[C@H](C)NC(=O)[C@@H](NC(=O)CCCCCN1C(=O)C=CC1=O)C(C)C]

Exemplary PBD-based antibody-drug conjugates include antibody-drug conjugates as shown below:

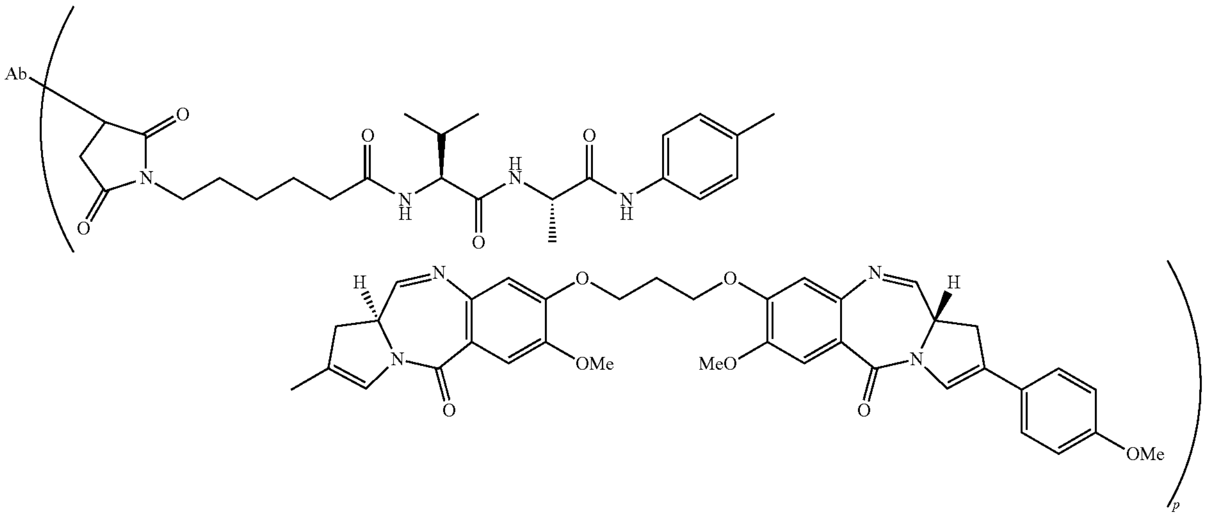

Indolinobenzodiazepines and oxazolidinobenzodiazepines differ in the number, type and position of substituents in their rings. As with the PBDs, two indolinobenzodiazepines or two oxazolidinobenzodiazepines units can be joined together to form dimers, e.g., through ether functionalities between the A rings of two monomeric units. As with the PBDs, an indolinobenzodiazepine dimer or oxazolidinobenzodiazepine dimer can be linked to an antibody at any position suitable for conjugation to a linker.

A benzodiazepine ADC that comprises a PBD dimer as the drug component can also be referred to as a PBD ADC. Similarly, a benzodiazepine ADC that comprises an indolinobenzodiazepine dimer as the drug component can be referred to as an IBD ADC and an ADC that comprises an oxazolidinobenzodiazepine dimer as the drug component can be referred as an OBD ADC. Typically benzodiazepine ADCs, including PBD ADCs, IBD ADCs and OBD ADCs, comprise a linker between the benzodiazepine drug and the antibody. The linker may comprise a cleavable unit (e.g., an amino acid or a contiguous sequence of amino acids that is or a salt thereof (e.g., pharmaceutically acceptable salt), wherein Ab is an antibody and drug-loading is represented by p, the number of drug-linker molecules per antibody. Depending on the context, p can represent the average number of drug-linker molecules per antibody, also referred to the average drug loading. P ranges from 1 to 20 and is preferably from 1 to 8. In some aspects, when p represents the average drug loading, p ranges from about 2 to about 5. In some aspects, p is about 2, about 3, about 4, or about 5. In some aspects, the antibody is conjugated to the drug linker via a sulfur atom of a cysteine residue. In some aspects the cysteine residue is a cysteine residue of the interchain disulfides of the antibody. In other aspects the cysteine residue is engineered into the antibody. In some aspects, the cysteine residue is engineered into the antibody at position 239 (IgG1) as determined by the EU index (Kabat, *Sequences of Proteins of Immunological Interest* (National Institutes of Health, Bethesda, Md., 1987 and 1991)). Methods of making such ADCs are known in the art (see, for example, International Publication No. WO2011/130613).

Conjugation Process

The present invention is directed, inter alia, to methods for the removal of benzodiazepine drug-related impurities from a mixture comprising benzodiazepine ADCs and benzodiazepine-related impurities. A benzodiazepine drug-related impurity is any drug-related impurity arising from the conjugation reaction (including quenching step) of an antibody to a benzodiazepine drug or drug-linker. Benzodiazepine drug-related impurities include, for example, benzodiazepine dimer free drugs (including quenched drug), benzodiazepine drug-linkers, quenched benzodiazepine drug-linkers, or benzodiazepine drug-linker degradation products. Benzodiazepine drug-related impurities do not include benzodiazepine drugs or drug-linkers conjugated to antibodies (including antibody containing fragments thereof).

In some aspects of the present invention, an antibody (naked or conjugated to a linker) is contacted with a benzodiazepine drug-linker under conditions sufficient to form a conjugation reaction mixture comprising benzodiazepine ADCs and benzodiazepine drug-related impurities. In other aspects, an antibody (e.g., antibody-linker) is contacted with a benzodiazepine free drug under conditions sufficient to form a conjugation reaction mixture comprising benzodiazepine ADCs and benzodiazepine drug-related impurities. General methods of conjugating antibodies to linkers or drug-linkers are known in the art and are not described herein in detail. In some aspects, conjugation will be to the antibody's lysine residues. In other aspects, conjugation will be to a native or engineered cysteine present on the antibody (e.g., cysteine of an inter-chain disulfide or cysteine residue introduced into the heavy or light chain of the antibody). In some aspects, the engineered cysteine antibody will be reduced prior to contact with the benzodiazepine drug-linker, the antibody will be partially re-oxidized (i.e., re-oxidized as to the inter-chain disulfides but not as to the introduced cysteine) and the benzodiazepine drug-linker will be conjugated to the engineered cysteine on the partially re-oxidized antibody. In some such aspects, the engineered cysteine will be at position 239 (IgG1, EU index numbering as set forth in Kabat).

One of skill in the art will appreciate that the conditions used for conjugating the antibody to the drug or drug-linker will depend, in part, on the identity of the drug and linker. In general, conjugation reactions are conducted at a temperature of from about 0° C. to about 40° C. In some embodiments, the conjugation reaction is conducted at about 4° C. In some embodiments, the conjugation reaction is conducted at about 25° C. In some embodiments, the conjugation reaction is conducted at about 37° C. The conjugation reactions can be conducted for any suitable length of time. In general, the conjugation reaction mixtures are incubated under suitable conditions for anywhere between a few minutes and several hours. The reactions can be conducted, for example, for about 1 minute, or about 5 minutes, or about 30 minutes, or about 1½ hours, or about 4 hours, or about 12 hours, or about 24 hours. In general, conjugation reaction mixtures are formed with a pH ranging from about 6 to about 9. In some embodiments, the reaction mixture is formed with a pH of about 7 to about 8. Various buffering agents can be used to maintain a particular pH. Examples of suitable buffering agents include, but are not limited to, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), sodium citrate, sodium acetate, and sodium borate. Cosolvents (e.g., dimethyl acetamide, propylene glycol, dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), and chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)) can also be included as necessary. Buffers, cosolvents, salts, and chelators can be used at any suitable concentration, which can be readily determined by one of skill in the art. In general, buffers, cosolvents, salts, and chelators, can be included in reaction mixtures at concentrations ranging from about 1 μM to about 1M or even higher (e.g., 0-50% v/v depending on the co-solvent). Any suitable amount of benzodiazepine drug or drug-linker can be used for conjugation.

In some aspects, following conjugation of the antibody to the drug or drug-linker, and prior to activated charcoal filtration, a quenching agent will be used to quench any excess drug or drug-linker (e.g., unconjugated drug or drug-linker). A quenching agent is a reagent, other than an antibody, that is capable of abolishing the reactivity of a reactive moiety by covalently binding to the reactive moiety. One of skill in the art will appreciate that the quenching agent will be chosen based on the nature of the drug or linker. For example, a thiol such as β-mercapto ethanol or N-acetylcysteine can be used to quench excess drug-linker compounds containing a maleimido group. An amine such as glycine can be used to quench excess linker-drug compounds containing an N-hydroxysuccinimidyl ester. Typically, the quenching agent is used in excess with respect to the antibody and the drug-linker. In some aspects, excess benzodiazepine drug-linker is present in the reaction mixture and will be quenched. In such aspects, the benzodiazepine drug-related impurity will be a quenched benzodiazepine drug-linker. A quenched conjugation reaction mixture refers to a reaction mixture following conjugation of the antibody to the drug-linker and introduction of the quenching agent.

As an example of a PBD drug-linker synthesis, WO 2011/130613 describes a method of synthesizing a PBD drug-linker followed by conjugating the PBD drug-linker to an antibody. Briefly, antibodies in PBS containing 50 mM sodium borate at pH 7.4 are reduced with tris(carboxyethyl) phosphine hydrochloride (TCEP) at 37° C. Antibody interchain disulfides are reformed by oxidation with dehydroascorbic acid, leaving the engineered cysteines in the thiol form available for alkylation with drug linker. The reduced antibody is then alkylated with ~1.5 equivalents of maleimide drug-linker per antibody thiol, in the presence of sufficient co-solvent to solubilize the drug-linker. After about 90 min, the reaction is quenched by the addition of ~3 equivalents of N-acetyl cysteine relative to drug-linker.

Regardless of the conjugation methods used, benzodiazepine drug-related impurities will be present in the mixture. Generally, benzodiazepine drug-related impurities will be present in the mixture at levels of about 10 to 100 μM. Higher or lower concentrations of benzodiazepine drug-related impurities are contemplated. In some aspects, the benzodiazepine process impurity will be a quenched or un-quenched drug-linker, e.g., N-acetyl cysteine quenched drug-linker. In other aspects, the benzodiazepine process impurity will be a free benzodiazepine drug (i.e., benzodiazepine dimer not attached to a linker or antibody). In other aspects, the benzodiazepine drug-related impurity will be a benzodiazepine drug-linker degradation product, such as, for example, an oxidized or hydrolyzed derivative of the drug-linker.

In some aspects, following conjugation of the antibody or antibody-linker to the drug-linker or drug, as the case may be, and optional quenching of the benzodiazepine process intermediates, but prior to activated charcoal filtration, the mixture comprising benzodiazepine ADCs and benzodiazepine drug-related impurities will be filtered in order to reduce turbidity present in the process intermediate reaction mixture. The filtration can be via dead-end filtration (e.g., using filters with a pore size of 1 micron or smaller) or other filtration methods, including, for example, depth filtration. In other aspects, activated charcoal filtration will immediately follow conjugation, e.g., charcoal filtration will be the first purification step following conjugation and optional quenching.

Filtration with Activated Charcoal

Activated charcoal, also known as activated carbon, is charcoal that has been chemically or thermally activated. Activated charcoal has a very high surface area to mass ratio which enables physical adsorption of solute. Activated charcoal can come in bulk powder form or attached to a solid support. In some preferred embodiments, the activated charcoal used in the present invention is attached to a solid support. A solid support refers to an insoluble, functionalized material to which activated carbon can attach. Examples of solid supports include, for example, functionalized polymeric materials such as cellulose (e.g., cellulose fibers). The process of filtering a conjugation reaction mixture through an activated charcoal filter is referred to herein as activated charcoal filtration. Examples of charcoal filters that can be used in the present invention include charcoal-impregnated filters. Exemplary filters include the activated carbon cartridges and capsules sold by 3M (e.g., Zeta Plus™ filters), Pall, and Millipore. Passage of the mixture comprising the benzodiazepine drug-related impurities through the activated charcoal filter is conducted to clear the benzodiapine drug-related impurities from the ADC preparation.

Alternatively, the activated charcoal used in the present invention is in bulk powder form and is added, as a powder, or suspension, to the mixture to be purified. Passage of the mixture comprising the benzodiazepine ADCs, benzodiazepine drug-related impurities and activated charcoal through a filter clears the benzodiapine drug-related impurities from the ADC preparation.

It was surprisingly found by the present inventors that ADC loss during activated charcoal filtration occurred during the initial contact between the reaction mixture and the activated charcoal filter and continued recirculation or multiple discrete passages through the same filter did not result in additional ADC loss. In contrast, filtration through two separate filters resulted in increased ADC loss as compared to filtration through a single filter. Accordingly, activated charcoal filtration is preferably by single pass filtration through a single filter, multiple discrete filtrations through a single filter, or recirculation through a single filter. In embodiments wherein single pass filtration through a single filter is not sufficient to reduce the concentration of benzodiazepine drug-related impurities, activated charcoal filtration is preferably by multiple discrete filtrations through a single filter or recirculation through a single filter. Accordingly in preferred embodiments of the present invention, filtration through two or more separate filters is not performed. Generally, recirculation refers to passing a mixture through a filter by channeling the outlet stream from the filter directly to the inlet of the same filter, or to a reservoir, in which the reaction mixture is contained until the filtration process is complete. The stream can be channeled via an appropriate apparatus, such as a tube or pipe. In some aspects, when there is 10 g or less protein (i.e., benzodiazepine ADC) present in the mixture comprising benzodiazepine ADCs and benzodiazepine drug-related impurities (e.g., about 1, 2, 3, 4, 5, 6, 7, 8, or 9 g benzodiazepine ADC in the ADC mixture), recirculation through a single filter is preferred as compared to single pass filtration. In other aspects when there is greater than 10 g benzodiazepine ADC, or greater than 20 g benzodiazepine ADC in the mixture comprising benzodiazepine ADCs and benzodiazepine drug-related impurities, single pass filtration is preferred. In some aspects, when there is greater than 10 g benzodiazepine ADC, or greater than 20 g benzodiazepine ADC in the mixture comprising benzodiazepine ADCs and benzodiazepine drug-related impurities, multiple discrete filtration or recirculation is preferred as compared to single pass filtration.

Select parameters can be varied to alter the level of benzodiazepine drug-related impurities that can be removed from a mixture comprising them. It is known that the adsorption of solutes by carbon filtration is generally dependent on contact time, so that extraction efficiency depends on flux. Flow rate of the mixture through the activated charcoal filter can be increased or decreased as necessary to achieve a desired level of purity. In some aspects, the flow rate though the activated charcoal filter will be a flux of about 10 L/min/$m^2$ or lower, about 8 L/min/$m^2$ or lower, or about 6 L/min/$m^2$. In some aspects, the flux will be between about 3 L/min/$m^2$, or about 6 L/min/$m^2$ to about 10 L/min/$m^2$ or about 20 L/min/$m^2$. In some aspects, the flux will be between about 6 L/min/$m^2$ to about 10 L/min/$m^2$. In some aspects, the flux will be between about 6 L/min/$m^2$ to about 8 L/min/$m^2$.

Although a higher flow rate (e.g., a flow rate greater than about 6 L/min/$m^2$) might result in less clearance of the reaction process intermediates during activated charcoal filtration, the increase in flux can be compensated for by increasing the number of recirculation cycles. For example, whereas a desired level of clearance can be achieved at flow rate of 6 L/min/$m^2$ and 3 complete passages through a single filter, a flow rate of 12 L/min/$m^2$ might require 6 or more complete passages through a single filter. In some aspects, the reaction mixture will be recirculated from 2 to about 20 times over the activated charcoal filter, preferably from 5 to about 15 times over the activated charcoal filter. In some aspects, the filtration process will take from about 1 hour to about 5 hours, preferably from about 2 hours to about 4 hours to reduce the benzodiazepine process intermediates to an acceptable level. In some aspects, the filtration process will be completed when the concentration of benzodiazepine drug-related impurities has reached a target level. In some aspects, a target clearance level is about 1 μM or less, preferably 0.2 μM, or even 0.1 μM or less.

In some aspects, activated charcoal filtration will reduce the levels of benzodiazepine drug-related impurities (e.g., quenched drug-linkers) in the final reaction mixture to about 1 μM or less, preferably 0.2 μM, or even 0.1 μM or less.

In some aspects, the present invention provides benzodiazepine ADC formulations comprising 0.2 μM or less, 0.1 μM or less or 0.05 μM or less benzodiazepine drug-related impurities.

The present methods can be used for both small scale manufacturing efforts and large-scale efforts. For example, the present methods are applicable to a range of scales from milligrams to kilograms.

Following activated charcoal filtration, additional purification methods, including tangential flow filtration can be used to remove additional process-related impurities, including the non drug-related process impurities, e.g., chelators, solvents, quenching agents, and the like.

EXAMPLES

Figure 2:
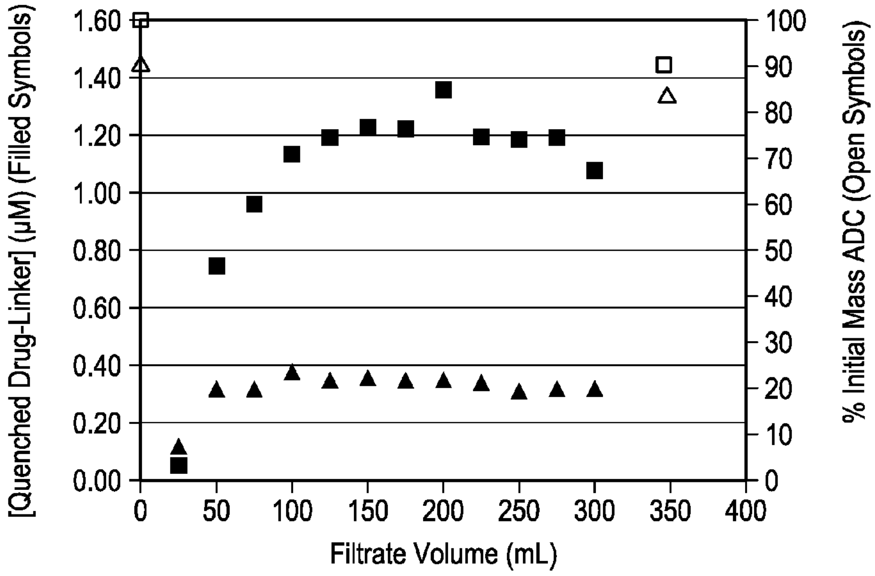
FIG. 2 provides a graph showing the concentration of quenched PBD drug-linker in the QCR mixture following filtration through one (filled squares) or two (filled triangles) Grade 3 3M Purification activated charcoal filters. Passage through a second filter provides additional clearance. Open square indicates the ADC concentration following the first filtration and open triangles indicates the ADC concentration following the second filtration. A fraction of the ADC is lost with each filtration step.
Figure 3:
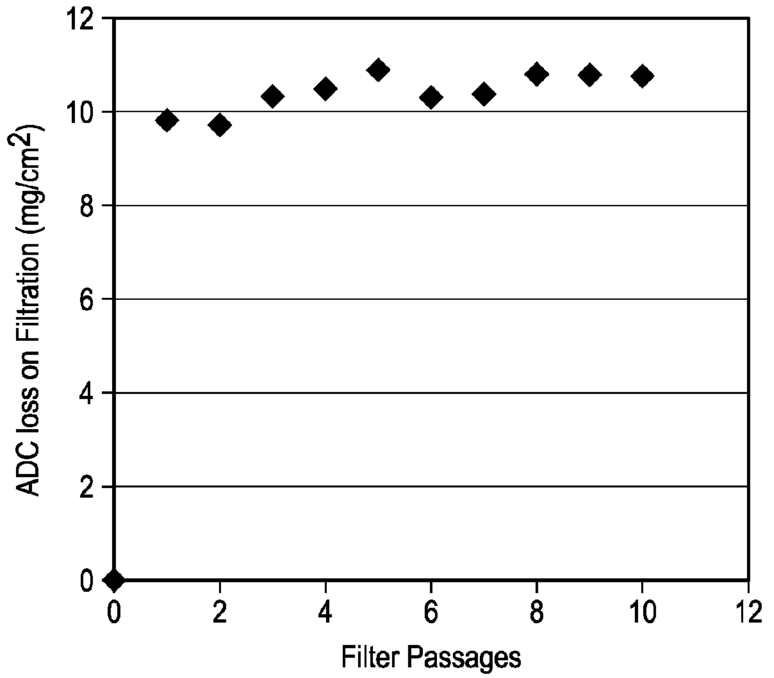
FIG. 3 illustrates the ADC loss during recirculation through the carbon filter. Essentially all ADC loss occurred during initial contact of the QCR mixture with the activated charcoal filter. Data are reported as mg ADC removed/$cm^2$ filter surface area.
Figure 4:
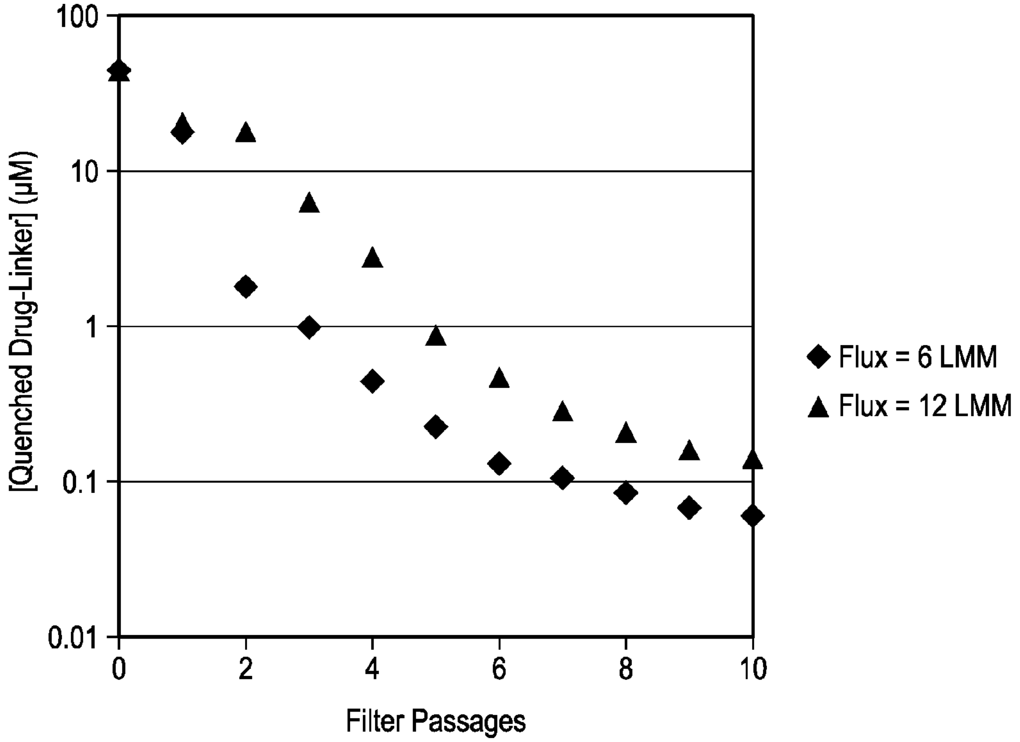
FIG. 4 provides a graph showing the clearance of quenched PBD drug-linker during re-circulation over an activated charcoal filter at different fluxes. The data indicate that for a given number of passages, lower flux provides better clearance.

Experiments in FIGS. 1, 2, and 3 were conducted using Grades 3 or 5 3M Purification Zeta Plus 13.5 $cm^2$ activated charcoal discs mounted in a stainless steel holder. Experiments in Table 1 and FIG. 4 were conducted using 3M Purification Zeta Plus BC25 Grade 5 Activated Charcoal Capsule Filters. Experiments in FIG. 5 were conducted using Zeta Plus Activated Carbon Capsule Filters, BC25 or BC1000 (650 $cm^2$) as indicated in the graph legend. Protein loading is in the range of 700 $g/m^2$ or less, and flux was ~6 LMM or as indicated.

The carbon filters were used according to the vendor's instructions. Carbon filters were flushed prior to use to clear unsequestered carbon powder, then equilibrated with the QCR buffer medium (50 mM Tris/5 mM EDTA, pH 7.5). Flow of the QCR was maintained by a peristaltic pump. Effluent was sampled from the flow immediately after passing through the filter.

Benzodiazepine drug-related impurities were quantified by RP-HPLC. Drug-related peaks were detected and quantified by UV.

followed by SEM dilactam reduction to reveal the imine functional groups. PBD dimers 5-8 and 10 are prepared in the same manner from C5-tethered bis-triflate intermediate 8b in WO2011/130613 A1. PBD dimers 11-15 containing esters or carboxylic acids in the C2 aryl groups can be accessed using the methods described in WO2011/130613 A1 with minor modifications. PBD dimer 13 can be prepared from the C3-tethered bis-triflate intermediate 8a in WO2011/130613 A1. The bis triflate is desymmetrized via Suzuki coupling with an appropriately functionalized boronic acid or pinacol boronate to install the C2 aryl group bearing the amino functional group. The resulting monotriflate is then reduced with lithium triethylborohydride to the SEM carbinol, which is then carried forward to the second Suzuki coupling to install the C2 aryl group containing the methyl ester. Finally, the SEM carbinols are converted to imines via stirring on silica gel for 3 days, as described in WO2011/130613 A1. PBD dimers 12, and 14 can be prepared in the same way starting with C5-tethered bis triflate 8b in WO2011/130613 A1. Conversion of the PBD esters to the free carboxylic acids (11 and 15) could be achieved via saponification.

The drug-linker referred to in the examples and the synthesis thereof is described in WO2011/130613 and has the following structure:

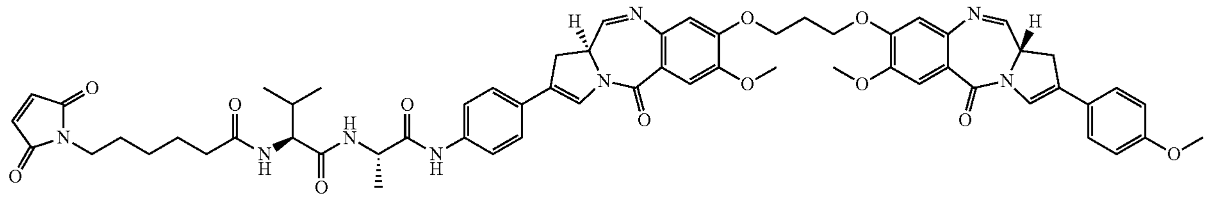 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

The quenched drug-linker referred to in the following examples has the following structure:

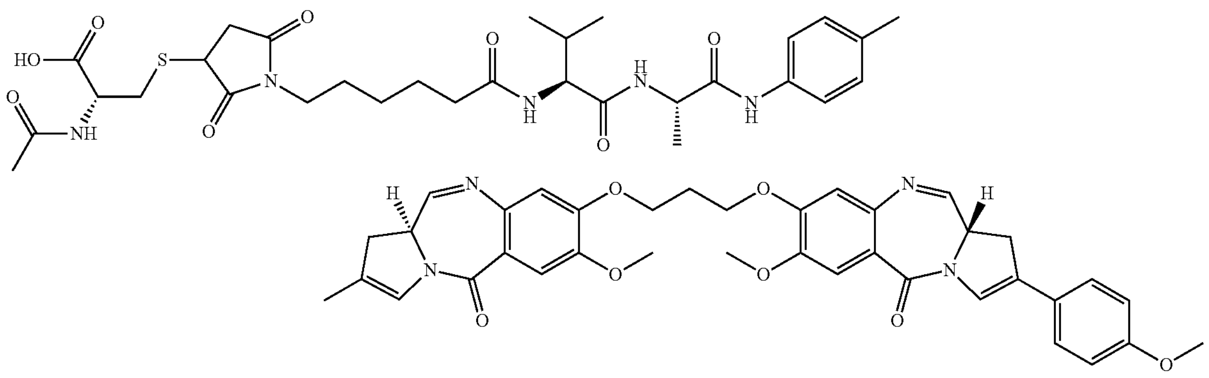

Back-pressure created by the filter was monitored to ensure the pressure did not exceed the manufacturer's recommended differential pressure of 35 psi.

PBD dimers 1-4 and the synthesis thereof are described in WO2011/130613. PBD dimers 5-10 and 16 can be synthesized using the methods described in WO2011/130613 A1. Briefly, PBDs dimers 9 and 16 are accessible through the C3-tethered bis-triflate intermediate 8a in WO2011/130613 A1. The desired C2 aryl groups as boronic acids or pinacol boronates are introduced in sequential Suzuki couplings, The 2H12 antibody is an engineered IgG1 antibody having a cysteine residue substitution at position 239 of the heavy chain. The sequence of the 2H12 heavy and light chain variable regions and constant regions are provided in SEQ ID NOs:1-4.

| | | |
|---|---|---|
| Humanized 2H12 VL | DIQMTQSPSSLSASVGDRVTINCKA SQDINSYLSWFQQKPGKAPKTLIYR | 1 |

-continued

| | | |
|---|---|---|
| | ANRLVDGVPSRFSGSGSGQDYTLTI SSLQPEDFATYYCLQYDEFPLTFGG GTKVEIK | |
| Humanized 2H12 VH | QVQLVQSGAEVKKPGASVKVSCKAS GYTFTNYDINWVRQAPGQGLEWIGW IYPGDGSTKYNEKFKAKATLTADTS TSTAYMELRSLRSDDTAVYYCASGY EDAMDYWGQGTTVTVSS | 2 |
| Human light chain constant region | TVAAPSVFIFPPSDEQLKSGTASVV CLLNNFYPREAKVQWKVDNALQSGN SQESVTEQDSKDSTYSLSSTLTLSK ADYEKHKVYACEVTHQGLSSPVTKS FNRGEC | 3 |
| Human heavy chain constant region, S239C (no C-term K) | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPCVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPG | 4 |

The quenched conjugation reaction mixture (QCR) used in the following filtration experiments was prepared as follows: Anti-CD33 antibody, h2H12 IgG1, having an introduced cysteine at position 239 (EU index numbering) was reduced, partially re-oxidized (i.e., re-oxidized as to interchain disulfides), and conjugated to the PBD drug-linker using methods described in WO 2011/130613 to form an ADC. The PBD drug-linker was conjugated to the partially re-oxidized antibody via the introduced cysteine residues (average of 2 drug-linkers per antibody). After conjugation, the reaction mixture was quenched by the addition of N-acetyl cysteine and filtered using dead-end filtration.

Example 1

Purification of Benzodiazepine ADCs Using Tangential Flow Filtration

The quenched drug-linker was purified from the QCR using constant volume diafiltration. The quenched conjugation reaction mixture was introduced into the tangential flow filtration device. The quenched conjugation reaction mixture comprises of Tris, NaCl and 50% propylene glycol. The tangential flow filtration buffer also comprises Tris, NaCl and 50% propylene glycol. After the ultrafiltration/diafiltration sequence, 1.1 uM benzodiazepine drug-related impurity remained in the mixture with the clearance stalling after four diavolumes (data not shown).

Example 2

Single Pass Filtration of Benzodiazepine ADCs Through a Grade 5 Activated Charcoal 3M Purification Filter Activated charcoal filters (25 $cm^2$ 3M Purification Zeta Plus BC25 Grade 5 activated Charcoal Capsule filter) were investigated for benzodiazepine drug-related impurity removal efficiency and protein recovery. Prior to filtration, the filter was equilibriated and purged with air. The concentration of quenched drug-linker remained constant throughout the filtration (FIG. 1). The QCR contained 35.9 μM quenched drug-linker demonstrating that carbon filtration reduced the level of quenched drug-linker by about 98%. Determination of protein concentration at the beginning and end of this filtration indicated a loss of approximately 7% of the ADC.

Example 3

Single Pass Filtration of Benzodiazepine ADCs Through a Grade 3M Purification Activated Charcoal Filter An aliquot of QCR was passed through a Grade 3 carbon filter (FIG. 2, Filtration 1, filled squares). In this case, the filter was not purged with air after equilibration. Dilution by the residual equilibration buffer was observed in the first 4 samples, but subsequent samples retained a relatively constant ~1.2 μM quenched drug-linker. Recovery was not improved by leaving equilibration buffer in the filter prior to filtration. Grade 5 carbon filters showed better adsorption of PBDs than grade 3 carbon filters.

The flow-through from this Grade 3 carbon filtration was then passed over a 2nd grade 3 carbon filter under identical conditions. The result (FIG. 3, Filtration 2, filled triangles) indicated that re-filtration did adsorb additional quenched drug-linker, reducing its concentration to about 0.4 μM, but the 2nd filter also adsorbed additional ADC. Approximately 7% of the ADC was lost with passage through each grade 3 carbon filter.

Example 4

Single Pass Filtration, Multiple Discrete Filtrations, and Re-circulation of Benzodiazepine ADCs Through a Grade 5 3M Purification Activated Charcoal Filter Re-circulation, as opposed to a single-pass filtration, was investigated as a potentially more efficient mode of clearance of PBDs. First, an ADC recovery study (FIG. 3), was performed to determine the feasibility of re-circulation through an activated charcoal filter. If the ADC concentration continued to drop as the solution re-circulated through the filter, then re-circulation would not be a viable mode by which to increase PBD clearance. However, the results showed that almost all of the ADC loss occurred at the initial contact between QCR solution and activated charcoal filter, and continued re-circulation did not result in additional ADC loss.

Three modes of filtration were investigated for drug clearance efficiency and ADC recovery: re-circulation through a single filter, 3 complete passages through a single filter (3 discrete filtrations), and single pass filtration through 2 separate filters. For the 3 discrete filtrations, the entire batch was passed through the filter and collected in a receiving container. The batch was then passed again through the same filter and collected in a receiving container. Finally the batch was passed through the same filter a 3rd time and collected in the final vessel. All 3 filtration strategies provided good quenched drug-linker clearance (Table 1). However, a single past through two different filters in series gave unacceptable ADC loss. Re-circulation and filtration 3 times through a single filter gave equivalent levels of clearance, with comparable ADC recovery.

TABLE 1

Comparison of Modes of Filtration with Cuno Grade 5 Activated Carbon Filters.

| Mode | Re-circulation (10 batch volumes) | Double Filtration (2 separate filters) | 3 × 1 Filter (three times through a single filter) |
|---|---|---|---|
| Final level of quenched drug-linker achieved (μM) | 0.06 | 0.08 | 0.10 |
| % Recovery | 82.1 | 73.4 | 85.7 |

Example 5

Changes in Flux and its Effect on Purification

The results provided in Table 1 were obtained at a flux of 6 LMM. To determine whether the same quenched drug-linker extraction could be obtained at higher flux—to shorten process time—an additional aliquot of the QCR used for the experiments in Table 1 was re-circulated over an identical carbon filter at 12 LMM. The results (FIG. 4) showed that clearance was less effective with the increased flux.

Example 6

Protein Loading

Figure 5:
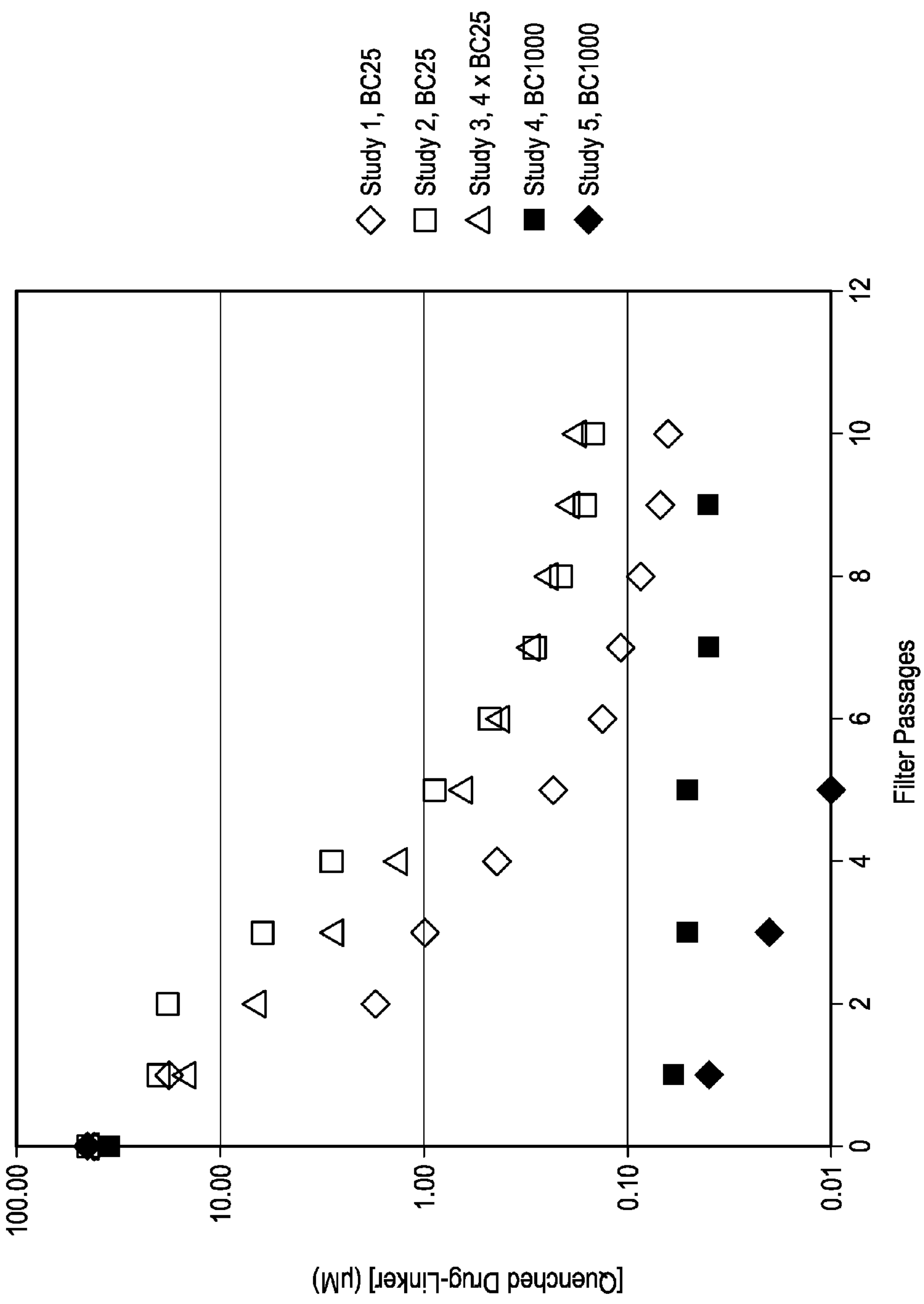
FIG. 5 provides a graph showing the clearance of quenched PBD drug-linker from the quenched conjugation reaction mixture using different filters and protein loading concentrations.
Figure 6:
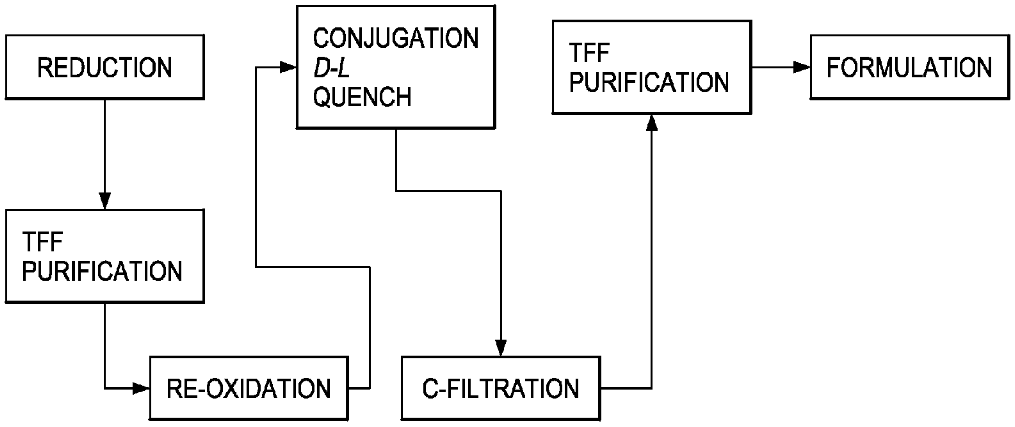
FIG. 6 provides an exemplary purification scheme for the benzodiazepine ADCs FIG. 7 provides an exemplary purification scheme for the benzodiazepine ADCs
Figure 7:
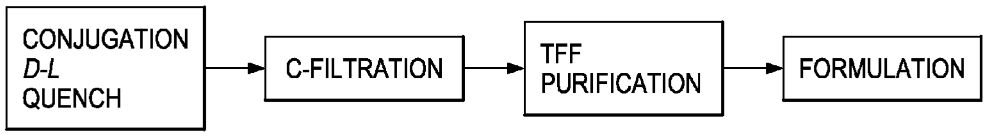

As seen in FIG. 5, recirculation through a single filter helped clear quenched drug-linker to levels less than 0.1 μM when using a BC25 filter (protein loading concentrations of less than 10 g) or a BC1000 filter (protein loading concentration of greater than 10 g). In one experiment using the BC1000 filter (protein loading concentration of greater than 10 g), one pass was sufficient to reduce quenched drug-linker levels to less than 0.1 μM.

What is claimed:

1. A method of removing benzodiazepine drug-related impurities from a mixture comprising benzodiazepine ADCs and benzodiazepine drug-related impurities comprising passing the mixture through an activated charcoal filter.

2. The method of claim 1 further comprising the steps of (i) contacting an antibody with a benzodizepine drug-linker under conditions sufficient to form a mixture comprising benzodiazepine ADCs, and (ii) contacting the mixture with a quenching agent to form quenched benzodiazepine drug-linkers.

3. The method of claim 1 further comprising the steps of (i) contacting an antibody conjugated to a linker with a benzodizepine drug under conditions sufficient to form a mixture comprising benzodiazepine ADCs and benzodiazepine drug-related impurities.

4. The method of claim 1 wherein the benzodiazepine drug-related impurities are quenched drug-linkers.

5. The method of claim 1 wherein the benzodiazepine drug-related impurities are unconjugated drugs.

6. The method of claim 1 wherein the activated charcoal is attached to a solid support.

7. The method of claim 1 wherein filtration is via single pass filtration or recirculation through a single filter.

8. The method of claim 1 wherein filtration is via multiple discrete filtrations through a single filter.

9. The method of claim 7 wherein filtration is via recirculation through a single filter when there is 10 g or less benzodiazepine ADC in the mixture and filtration is via single pass filtration when there is greater than 10 g benzodiazepine ADC in the mixture.

10. The method of claim 7 wherein there is greater than about 20 g benzodiazepine ADC in the mixture and filtration is via single pass filtration.

11. The method of claim 1 wherein the flux is between about 3 $L/min/m^2$ and 20 $L/min/m^2$.

12. The method of claim 11 wherein the flux is between about 6 $L/min/m^2$ and 20 $L/min/m^2$.

13. The method of claim 7 wherein filtration is via recirculation through a single filter and wherein the mixture comprising benzodiazepine ADCs and benzodiazepine drug-related impurities is recirculated from 3 to about 20 times through a single filter.

14. The method of claim 1 wherein the benzodiazepine drug-related impurities are reduced to a level of about 1 μM or less.

15. The method of claim 14 wherein the benzodiazepine drug-related impurities are reduced to a level of about 0.5 μM or less.

16. The method of claim 1 wherein the activated charcoal filter is an activated carbon cartridge or capsule.

17. The method of claim 1 wherein prior to activated charcoal filtration, the mixture is filtered via dead-end filtration or depth filtration.

18. The method of claim 1 wherein following activated charcoal filtration, the resultant mixture is subjected to one or more additional purification processes.

19. The method of claim 1 wherein the benzodiazepine ADCs comprise pyrrolobenzodiazepine dimers, indolinobenzodiazepine dimers, or oxazolidinobenzodiazepine dimers.

20. The method of claim 1 wherein the antibody is conjugated to the benzodiazepine drug via a cysteine residue which is engineered into the antibody at position 239 of the IgG1 chain according to EU index numbering.

21. The method of claim 20 wherein there are an average of about 2 drug-linkers per antibody in the mixture.

* * * * *

SEQUENCE LISTING

```
<160> NUMBER OF SEQ ID NOS: 4

<210> SEQ ID NO 1
<211> LENGTH: 107
<212> TYPE: PRT
<213> ORGANISM: Artificial
<220> FEATURE:
<223> OTHER INFORMATION: Humanized 2H12 VL

<400> SEQUENCE: 1

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105


<210> SEQ ID NO 2
<211> LENGTH: 117
<212> TYPE: PRT
<213> ORGANISM: Artificial
<220> FEATURE:
<223> OTHER INFORMATION: Humanized 2H12 VH

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60
```

```
Lys Ala Lys Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
        115


<210> SEQ ID NO 3
<211> LENGTH: 106
<212> TYPE: PRT
<213> ORGANISM: Artificial
<220> FEATURE:
<223> OTHER INFORMATION: Human light chain constant region

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 4
<211> LENGTH: 329
<212> TYPE: PRT
<213> ORGANISM: Artificial
<220> FEATURE:
<223> OTHER INFORMATION: Human heavy chain constant region, S239C (no
      C-term K)

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125
```

-continued

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```